United States Patent
Mocikat et al.

(12)
(10) Patent No.: US 6,322,787 B1
(45) Date of Patent: Nov. 27, 2001

(54) INDUCTION OF AN ANTI-TUMOR IMMUNITY BY REDIRECTING TUMOR CELLS AGAINST ANTIGEN-PRESENTING CELLS

(75) Inventors: Ralph Mocikat, Gauting; Horst Lindhofer, Groebenzell, both of (DE)

(73) Assignee: GSF Forschungszentrum fur Umwelt und Gesundheit GmbH, Neuherberg (DE)

( * ) Notice: Subject to any disclaimer, the term of this patent is extended or adjusted under 35 U.S.C. 154(b) by 0 days.

(21) Appl. No.: 09/369,498

(22) Filed: Aug. 5, 1999

(30) Foreign Application Priority Data

Aug. 6, 1998 (DE) .............................................. 198 35 633

(51) Int. Cl.[7] ........................ A61K 39/395; A61K 39/40; A61K 39/42; C12N 5/06; C12N 5/16
(52) U.S. Cl. .................................... 424/153.1; 424/130.1; 424/133.1; 424/134.1; 424/152.1; 424/153.1; 424/155.1; 435/326; 435/328; 435/330; 435/332; 435/344; 435/346; 435/354; 435/440; 435/449; 435/451; 435/452
(58) Field of Search ..................................... 435/326, 328, 435/330, 332, 344, 346, 354, 440, 449, 451, 452; 424/130.1, 133.1, 134.1, 152.1, 153.1, 155.1

(56) References Cited

PUBLICATIONS

Kearney, et al. A new mouse myeloma cell line that has lost immunglobulin expression but permits the construction of antibody–secreting hybrid cell lines. The Journal of Immunology 123(4):1548–1550, Oct. 1979.*
Shulman et al. A better cell line for making hybridomas secreting specific antibodies. Nature 276:269–270, 1978.*
Harlow and Lane. Antibodies, A laboratory manual, pp.96–99, 1988.*
ATCC Cell Lines and Hybridomas Catalog, 8th edition, pp. 413 and 419, 1994.*
Kearney, et al. A new mouse myeloma cell line that has lost immunglobulin expression but permits the construction of antibody–secreting hybrid cell lines. The Journal of Immunology 123(4):1548–1550, Oct. 1979.*
ATCC catalog. 8th edition, 1994.*
Harlow and Lane. Antibodies, A laboratory manual, pp.96–99, 1988.*

* cited by examiner

*Primary Examiner*—Sheela Huff
*Assistant Examiner*—Alana M. Harris
(74) *Attorney, Agent, or Firm*—Townsend and Townsend and Crew LLP

(57) ABSTRACT

According to the invention, there is provided a human or animal cell expressing an antibody directed against a surface antigen on an antigen-presenting cell (APC) and lacking parental tumor-derived immunoglobulin.

9 Claims, 1 Drawing Sheet

INDUCTION OF AN ANTI-TUMOR IMMUNITY BY REDIRECTING TUMOR CELLS AGAINST ANTIGEN-PRESENTING CELLS

Despite the progress in chemotherapy and radiotherapy in recent years, many malignant diseases in man still have an extraordinarily unfavourable prognosis. Frequently, these diseases can not be definitely cured because following a conventional therapy often residual malignant cells remain in the patient which later result in tumor recidivation. In this respect, great hopes have been placed on immunotherapeutical approaches by which the patient's immune system is induced to reject the tumor. It has been known that tumor-associated antigens exist on tumor cells and that in principle the immune system is capable of recognizing them and of attacking the malignant cells. However, tumors have developed several strategies which enable them to escape the immune response. This is possible by e.g. an insufficient presentation of tumor-associated antigens and/or insufficient activation of the tumor-specific T cells which generally exist. Enhancing antigen presentation is therefore a desirable object to achieve by an immunotherapeutical intervention.

DE 196 34 159.0 describes a method by which the B cell lymphoma immunoglobulin idiotype, i.e. an antigen which is absolutely tumor-specific in this disease, is directed against professional antigen-presenting cells (APCs). For this purpose, a so-called trioma is generated by fusing the lymphoma cells with a hybridoma expressing a specificity against APC surface molecules. This trioma secretes the tumor idiotype in the form of a bispecific immunoglobulin binding to APCs. Following internalization and processing of the idiotype, idiotype-derived peptides are presented on the APCs to the immune system. This results in a more efficient activation of T cells. Tumor-specific T cells may be generated by "professional" presentation of the tumor antigen on the APC in contrast to an incomplete presentation on the tumor cell. We have shown that for induction of a more efficient anti-tumor protection an injection of the modified cells is absolutely required. Treatment with the purified bispecific immunoglobulin failed to achieve an efficient anti-tumor immunity. We suggest that this may be due to an additional immunization against other tumor-associated antigens occuring after lysis of the trioma cells in the animal (or patient) treated. However, this method suffers from the disadvantage that it is applicable only to malignant diseases of B cells.

It is an object of the present invention to provide a novel means of inducing an anti-tumor immunity in a patient wherein said means shall be applicable not only to B cell tumors.

According to the invention said object has been solved by creating a tumor cell of human or animal origin expressing an antibody directed against a surface antigen on an antigen-expressing cell (APC) wherein the tumor cell lacks immunoglobulin derived from the parental tumor, i.e. the tumor cell itself originally did not contain any immunoglobulin. It is only by introduction of immunoglobulin-expressing genes encoding an antibody directed against a surface antigen on an antigen-expressing cell that the tumor cells are equipped with specific immunoglobulin.

Figure 1:
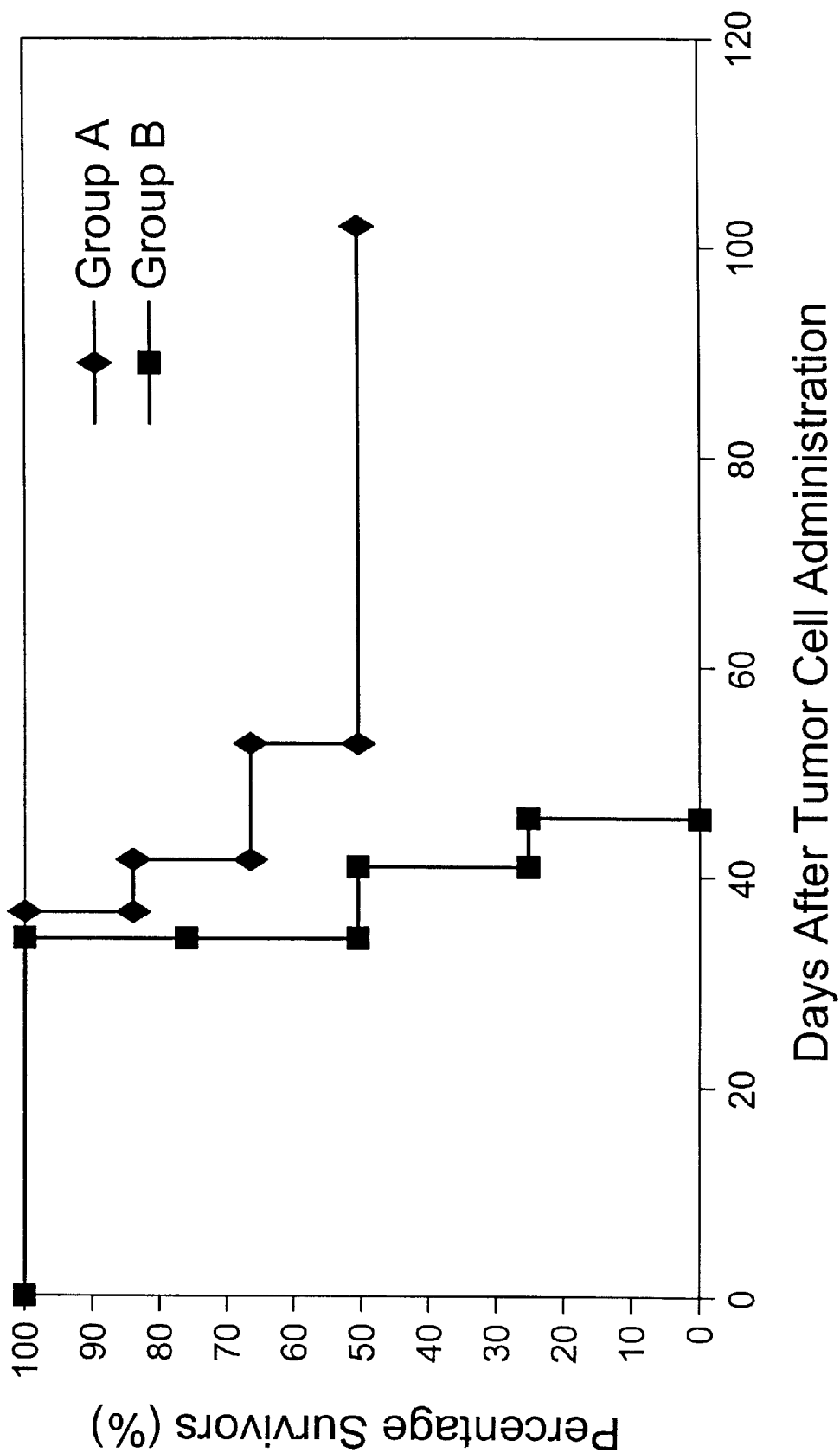
FIG. 1 shows experimental data providing evidence of tumor protection resulting from an implementation of the present invention.

With the genetically engineered tumor cell provided according to the invention, any tumor disease may be treated. Examples for tumor diseases are epithelial tumors, for example carcinomas, mesenchymal tumors, e.g. sarcomas, as well as hematopoietic tumors, such as leukemias and lymphomas. Among the lymphoproliferative diseases, even those of the T cell line or B cell line which produce no immunoglobulin may be treated.

By the expressed anti-APC antibody, the tumor cell altered according to the present invention preferably binds to Fc receptors, mannose-5-receptors or to MHC class II antigens as surface antigens.

Monocytes, macrophages and dendritic cells particularly serve as the antigen-presenting cells.

The tumor cell provided according to the present invention is administered to the patient in a therapeutically effective amount, preferably together with acceptable carriers and/or adjuvants, optionally after purification. The pharmaceutical composition provided according to the invention which comprises the tumor cell in a therapeutically effective amount is administered to the patient suffering from the tumor for example by injection or infusion.

The present invention demonstrates that for induction of an anti-tumor immunity an immunoglobulin idiotype such as the one present in B cell lymphomas is not absolutely required. This means that the principle of redirecting tumor antigens against APCs may be expanded also to all other tumors which do not express any immunoglobulin. This is an important finding since the tumors occuring most frequently in men are not derived from the B cell line. It is sufficient to bring the whole intact malignant cell into physical contact with the APCs. We have generated a trioma variant which has lost its tumor immunoglobulin and thus only carries the antibody directed against the APC surface molecule on its membrane. In principle, this variant contains all antigens of the parental lymphoma cell (exept the tumor-derived idiotype) so that following redirection of the whole cell to the APC all of the antigens should be processed and presented. Indeed, after immunization with this trioma variant, a lethal inoculum of wildtype tumor cells has been successfully rejected.

If this approach is applied to the clinical situation, malignant cells from a patient receiving a conventional therapy would be explanted, fused with an antibody-producing hybridoma and reintroduced into the patient. Alternatively, the immunoglobulin genes encoding anti-APC antibodies and having been isolated from the hybridoma are retransferred into autologous tumor cells. The genetically modified tumor cells, now expressing the antibody on their surface, are reintroduced into the patient following irradiation. In this manner, the whole tumor cell is targeted to the APCs which should result in phagocytosis and presentation of tumor antigens.

That the expression of an anti-APC specificity on the cell surface is necessary for complete generation of an anti-tumor immunity was directly demonstrated in another experiment in which a mixture was used for vaccination consisting of purified intact trioma protein and a trioma cell variant which while bearing the lymphoma idiotype was unable to bind to APCs due to loss of anti-APC specificity. Both the trioma cell variant and the purified soluble protein alone are only able to mediate marginal anti-tumor protection. However, it was demonstrated that by mixing the deficient cells and the intact protein the anti-tumor efficiency of intact trioma cells (i.e. 100% survival) could not be reconstituted. This finding also stresses the importance of direct physical contact between the trioma cell and APCs.

In the following, the invention will be described in more detail with respect to the Examples and the FIGURE.

However, the invention is not limited to these Examples but may be modified in the context of the following claims. Furthermore, according to continuing experience it is possible to apply the results obtained from an animal model also to humans.

EXAMPLES

1. The BALB/c mouse-derived B cell lymphoma A20 (ATCC TIB-208) is fused with anti-Fc receptor hybridoma 2.4G2 (ATCC HB-197). For this purpose, the hybridoma is rendered HAT-sensitive by cultivation in the presence of 8-azaguanine. $5 \times 10^6$ cells of the fusion partners are incubated in iodine acetamide for 30 minutes, washed and mixed with $1.5 \times 10^7$ HAT-sensitive cells. The fusion is performed by incubation with polyethylene glycol 1500 for two minutes. The cells are seeded into microtiter plates and after two to three days are subjected to selection in HAT medium. The hybrid cells are recloned by limiting dilution, and a variant which has lost the lymphoma idiotype is selected. It is shown by means of FACS analysis that these cells nevertheless still carry the 2.4G2 specificity on their surface.

2. BALB/c mice are injected twice i.p. with an interval of three weeks each time with $10^5$ cells expressing the 2.4G2 specificity on their surface. 7 days later an i.p. inoculation with $10^5$ wild type tumor cells (A20) is carried out. By the preimmunization, a long-lasting anti-tumor protection is achieved (see FIGURE; group A). In the control group without immunization (group B), the same number of tumor cells leads to tumor growth in 100% of the animals.

What is claimed is:

1. A modified tumor cell produced by a method comprising fusing a tumor cell that does not express immunoglobulin with a hybridoma cell that expresses an antibody against a surface antigen on an antigen-presenting cell, thereby causing said tumor cell to express an antibody directed against a surface antigen on said antigen-presenting cell.

2. A modified tumor cell produced by a method comprising introducing genes encoding antibody specific for an antigen presenting cell antibody into a tumor cell to express an antibody directed against a surface antigen on said antigen-presenting cell.

3. A modified tumor cell in accordance with claims 1 or 2 in which said antibody thus expressed by said modified tumor cell is membrane-associated.

4. A modified tumor cell in accordance with claims or 1 or 2 in which said tumor cell is a member selected from the group consisting of an epithelial tumor cell, a mesenchymal tumor cell, and a hematopoietic tumor cell.

5. A modified tumor cell in accordance with claims 1 or 2 in which said tumor cell is a member selected from the group consisting of a carcinoma cell, a sarcoma cell, a leukemic cell, and a lymphoma cell.

6. A modified tumor cell in accordance with claims 1 or 2 in which said surface antigen is a member selected from the group consisting of Fc receptors and MHC class II antigens.

7. A pharmaceutical preparation comprising modified tumor cell in accordance with claims 1 or 2 in a therapeutically effective amount and at least one pharmaceutically acceptable carrier, pharmaceutically acceptable adjuvant, or combination of such carrier and adjuvant.

8. A method for the preparation of a modified tumor cell, said method comprising fusing a tumor cell that does not express immunoglobulin with a hybridoma cell that expresses an antibody against a surface antigen on an antigen-presenting cell, thereby causing said tumor cell to express an antibody directed against a surface antigen on said antigen-presenting cell.

9. A method for the preparation of a modified tumor cell, said method comprising introducing genes encoding antibody specific for an antigen presenting cell antibody into a tumor cell that does not express immunoglobulin, thereby causing said tumor cell to express an antibody directed against a surface antigen on said antigen-presenting cell.

* * * * *